US006907102B1

(12) United States Patent
Sauer et al.

(10) Patent No.: US 6,907,102 B1
(45) Date of Patent: Jun. 14, 2005

(54) ITERATIVE RECONSTRUCTION METHODS FOR MULTI-SLICE COMPUTED TOMOGRAPHY

(76) Inventors: Ken Sauer, 18801 Burke, South Bend, IN (US) 46637; Charles A. Bouman, 40 Clay Ct., West Lafayette, IN (US) 47906; Jean-Baptiste Thibault, 1029 N. Jackson St., Apt. 1206A, Milwaukee, WI (US) 53202; Jiang Hsieh, 19970 W. Keswick Ct., Brookfield, WI (US) 53045

( * ) Notice: Subject to any disclaimer, the term of this patent is extended or adjusted under 35 U.S.C. 154(b) by 153 days.

(21) Appl. No.: 10/319,674

(22) Filed: Dec. 16, 2002

(51) Int. Cl.[7] .............................................. A61B 6/00
(52) U.S. Cl. ....................................... 378/19; 378/901
(58) Field of Search ........................... 378/4, 8, 15, 19, 378/901

(56) References Cited

U.S. PATENT DOCUMENTS 6,768,782 B1 * 7/2004 Hsieh et al. ................... 378/8

OTHER PUBLICATIONS

Allain et al., "Approche regularisee en reconstruction tomographique 3D helicoidale," *Proceedings of the 2001 GRETSI Symposium on Signal and Image Processing*, 2001, Toulouse, France (An english abstract is present on front page of reference).

Sauer et al., "A Local Update Strategy for Iterative Reconstruction from Projections" *IEEE Transactions on Signal Processing* vol. 41, No. 2, Feb. 1993.

Bouman et al., "A Unified Approach to Statistical Tomography Using Coordinate Descent Optimization" *IEEE Transactions on Image Processing* vol. 5, No. 3, Mar. 1996.

Herbert et al., "A Generalized EM Algorithm for 3–D Bayesian Reconstruction From Poisson Data Using Gibbs Priors" *IEEE Transactions on Medical Imaging* vol. 8, No. 2, Jun. 1989.

Kak et al., "Algebraic Reconstruction Algorithms" *Principles of Computerized Tomographic Imaging* (IEEE Press, 1988), pp. 275–296 Note: *Principles of Computerized Tomographic Imaging* is now published by the Society for Industrial and Applied Mathmatics.

Kak et al., "Algorithms for Reconstruction with Nondiffracting Sources" *Principles of Computerized Tomographic Imaging* (IEEE Press, 1988), pp. 49–112 Note: *Principles of Computerized Tomographic Imaging* is now published by the Society for Industrial and Applied Mathematics.

Shepp et al., "Maximum Likelihood Reconstruction for Emission Tomography" *IEEE Transactions on Medical Imaging* vol. MI–1, No. 2, Oct. 1982.

* cited by examiner

*Primary Examiner*—Edward J. Glick
*Assistant Examiner*—Courtney Thomas
(74) *Attorney, Agent, or Firm*—Jagtiani + Guttag

(57) ABSTRACT

A multi-slice computed tomography imaging system is provided including a source that generates an x-ray beam and a detector array that receives the x-ray beam and generates projection data. A translatable table has an object thereon and is operable to translate in relation to the source and the detector array. The source and the detector array rotate about the translatable table to helically scan the object. An image reconstructor is electrically coupled to the detector array and reconstructs an image in response to the projection data using a computed tomography modeled iterative reconstruction technique. The iterative reconstruction technique includes determining a cross-section reconstruction vector, which approximately matches the projection data via a computed tomography model. Methods for performing the same are also provided including accounting for extended boundary regions.

22 Claims, 3 Drawing Sheets

ITERATIVE RECONSTRUCTION METHODS FOR MULTI-SLICE COMPUTED TOMOGRAPHY

CROSS-REFERENCE TO RELATED APPLICATIONS

The present invention is related to U.S. patent application Ser. No. 10/319,689 entitled "An Iterative Method for Region-of-Interest Reconstruction" filed simultaneously herewith and incorporated by reference herein.

BACKGROUND OF THE INVENTION

1. Field of the Invention

The present invention relates generally to multi-slice computed tomography (CT) imaging systems, and more particularly, to an apparatus and methods of reconstructing an image using iterative techniques.

2. Description of the Prior Art

A computed tomography (CT) imaging system typically includes an x-ray source that projects a fan-shaped x-ray beam through an object being imaged, such as a patient, to an array of radiation detectors. The beam is collimated to lie within an X-Y plane, generally referred to as an "imaging plane". Intensity of radiation from the beam received at the detector array is dependent upon attenuation of the x-ray beam by the object. Attenuation measurements from each detector are acquired separately to produce a transmission profile.

The x-ray source and the detector array are rotated within a gantry and around the object to be imaged so that a projection angle at which the x-ray beam intersects the object constantly changes. A group of x-ray attenuation measurements, it al., integral projection data, from the detector array at one gantry angle is referred to as a "view". A "scan" of the object comprises a set of views made at varying projection angles, during one revolution of the x-ray source and detector array.

In an axial scan, the projection data is processed to construct an image that corresponds to a two-dimensional slice taken through the object. For discrete slices, iterative reconstruction of a full field of view may be performed in order to increase image quality. Iterative reconstruction refers to a method which forms an image by repeatedly adjusting an existing estimate according to the quality of a match between measured data and simulated measurements from a current estimate of the image. The quality of the match may also be affected by consideration of the characteristics of the image alone, such as its smoothness and/or satisfaction of a pre-established model. Multiple iterations are performed to create a resulting reconstructed image that approximately matches the acquired projection data. A full set of reconstructed images is referred to as a 3-D reconstruction, since the set is formed into a three dimensional representation of the object with each image pixel or picture element corresponding to a single voxel or volume element in the 3-D reconstruction.

To reduce the total scan time required for multiple slices, a "helical" scan may be performed. Helical scan techniques allow for large volumes to be scanned at a quicker rate using a single photon source. To perform a "helical" scan, the patient is moved along the z-axis, the axis about which the gantry rotates, synchronously with the rotation of the gantry, while data for a prescribed number of slices are acquired. Such a system generates a single helix from a fan beam helical scan. The helix mapped out by the fan beam yields projection data from which images in each prescribed slice may be reconstructed. In addition to reducing scan time, helical scanning provides other advantages such as better use of injected contrast, improved image reconstruction at arbitrary locations, and better three-dimensional images.

Unfortunately, conventional helical scan CT has several associated disadvantages. Three-dimensional reconstruction may be produced by a series of two-dimensional reconstruction slices, acquired for discrete positions or acquired via a continuous scan of the patient along the z-axis. Acquisition of helical scan data for discrete positions is a limitation in further decreasing scan time. For continuous scans, a scan pattern in which the z-position varies linearly with rotation angle is produced. The scan pattern is interpolated to form two-dimensional planar arrays that approximate scan data acquired when translating the table in discrete steps rather than continuous translation. The interpolation of the helical scanned data introduces errors since the interpolated data does not exactly match true projection values. The errors result in artifacts in the reconstructed image, particularly near sharp discontinuities.

Conventional methods for tomographic image reconstruction in single planes from axial mode data may be found in Avinash C. Kak and Malcolm Slaney, "Principles of Computerized Tomographic Imaging," Classics in Applied Mathematics, 33, SLAM, 2001, ISBN:089871494X, the entire contents and disclosure of which is hereby incorporated by reference, having been applied especially to X-ray CT since the 1970's. One of the earliest iterative methods for reconstruction, algebraic reconstruction technique (ART), is also discussed in Avinash C. Kak and Malcolm Slaney, "Principles of Computerized Tomographic Imaging," Classics in Applied Mathematics, 33, SIAM, 2001, ISBN:089871494X, the entire contents and disclosure of which is hereby incorporated by reference. References such as L. Shepp and Y. Vardi, "Maximum Likelihood Reconstruction for Emission Tomography," IEEE Transactions on Medical Imaging, vol. MI-1, no. 2, pp. 113–122, October 1982, and T. Hebert and R. Leahy, "A Generalized EM Algorithm for 3-D Bayesian Reconstruction from Poisson data Using Gibbs Priors," IEEE Transactions on Medical Imaging, vol. 8 no. 2, pp. 194–202, June 1989, the entire contents and disclosures of which are hereby incorporated by reference, and their references introduce some key elements of statistically based iterative reconstruction. In references such as K. Sauer and C. A. Bouman, "A Local Update Strategy for Iterative Reconstruction from Projections," IEEE Transactions on Signal Processing, vol. 41, no. 2, pp. 534–548, February 1993, and C. A. Bouman and K. Sauer, "A Unified Approach to Statistical Tomography Using Coordinate Descent Optimization," IEEE Transactions on Image Processing, vol. 5, no. 3, pp. 480–492, March 1996, the entire contents and disclosures of which are hereby incorporated by reference, fundamental concepts are introduced which have here been extended to three-dimensional CT, particularly the numerical method subsequently referred to as "iterative coordinate descent." Reconstruction has also been performed in single-slice helical scan CT with Bayesian statistical methods, but that work does not include multi-slice scanning. See Marc Allain, Yves Goussard and Jerome Idier, "Approche regularisee en reconstruction tomographique 3D helicoidale," Proceedings of the 2001 GRETSI Symposium on Signal and Image Processing, 2001, Toulouse, France, the entire contents and disclosure of which is hereby incorporated by reference.

Another method for reducing scan time is referred to as multi-slice helical scan. In multi-slice helical scan, the detector array extends along the z-axis. Typically, the detector array contains multiple rows, with each row corresponding to a different position in z, and a different measured slice. Some of the detector rows measure projections that exist outside an image plane. Scanned data is then interpolated to form two-dimensional planar arrays that approximate scan data acquired from single slice helical scans taken with the table translating in discrete steps rather than continuous translation. The interpolation of the multi-slice helical scanned data introduces errors since the interpolated data does not exactly match true measured data. The errors result in artifacts in the reconstructed image, particularly near sharp discontinuities.

Also in conventional helical scan CT, algorithms tend to modify and warp an image plane in order to match the projection data. The modifications and warping of the imaging plane causes blurring of the reconstructed image.

Sharp discontinuities typically occur near regions with important detail such as an interface of bone and tissue. The sharp discontinuities may also be due to the presence of dense objects, such as metal clips or other dense objects known in the art. The artifacts may therefore obscure important details of the dense objects and sharp discontinuities and may extend radially, obscuring other regions of the reconstruction.

A disadvantage of iterative reconstruction for multi-slice helical scans is that boundary conditions may be difficult to model when the object being scanned extends beyond a scanned range. Regions outside the field of view (FOV) may affect measurements that project obliquely through the object in a z direction, especially for measured values of projections for slices near the boundaries of the FOV. In helical scan CT systems, projections typically pass through more than one plane in the z direction, creating a cross-plane effect, due to detector arrays extending along the z-direction. The cross-plane effect is particularly strong for multi-slice helical CT systems that use relatively high pitch values. Errors in the summation for a particular projection occur when the projection passes through the FOV, but due to the cross plane effect, also passes through regions outside the FOV. Such projections may result in an erroneous value of a summation computed for a corresponding detector. Therefore, iterative reconstruction for an object extending outside the scanned range produces a reconstructed image containing significant artifacts near boundaries of the FOV.

It would therefore be desirable to provide an iterative method of reconstructing an image for a multi-slice helical scan CT imaging system that provides increased scanning speed, accounts for portions of a scanned object outside a scanned range, and minimizes blurring and artifacts in a reconstructed image.

SUMMARY OF THE INVENTION

The present invention provides an apparatus and methods of computing image reconstructions using iterative techniques for a multi-slice computed tomography (CT) imaging system. A multi-slice CT imaging system is provided including a source that generates an x-ray beam and a detector array that receives the x-ray beam and generates projection data. A translatable table has an object thereon and may be operable to translate in relation to the source and the detector array. The source and the detector array rotate about the translatable table to helically scan the object. An image reconstructor may be electrically coupled to the detector array and reconstructs an image in response to the projection data using a computed tomography modeled iterative reconstruction technique. An iterative reconstruction technique of the present invention includes determining a cross-section reconstruction vector, which approximately matches the projection data via a computed tomography model. Methods for performing the same are also provided including accounting for extended boundary regions.

One of several advantages of the present invention is that it accounts for direct geometry of a multi-slice scan CT imaging system, thereby reducing and potentially eliminating artifacts.

Another advantage of the present invention is that it uses a CT model in order to match projection data. A CT model minimizes approximation errors and prevents warping of image planes.

Furthermore, the present invention accounts for boundary conditions, therefore minimizing artifacts near boundary regions of a reconstructed image.

According to a first broad aspect of the present invention, there is provided an imaging system comprising: a source generating a x-ray beam; a detector array receiving the x-ray beam and generating projection data; a translating table having an object thereon and operable to translate in relation to the source and the detector array; the source and the detector array rotating about the translating table to helically scan the object; an image reconstructor electrically coupled to the detector array and reconstructing an image in response to the projection data using a computed tomography modeled iterative reconstruction technique comprising determining a cross-section reconstruction vector, which approximately matches the projection data via a computed tomography model, wherein the imaging system is a multi-slice computed tomography imaging system.

According to a second broad aspect of the invention, there is provided a method of reconstructing an image of an object for a multi-slice computed tomography imaging system comprising: providing projection data; and performing a computed tomography modeled iterative reconstruction technique to reconstruct the image in response to the projection data comprising determining a cross-section reconstruction vector, which approximately matches the projection data via a computed tomography model.

According to a third broad aspect of the invention, there is provided a method of reconstructing an image comprising: helically scanning the object to acquire projection data; and performing a computed tomography modeled iterative reconstruction technique to reconstruct the image in response to the projection data comprising; determining a cross-section reconstruction vector, which approximately matches the projection data via a computed tomography model; incorporating extended boundary regions into the computed tomography model; and minimizing a cost function over the extended boundary regions during the iterative reconstruction technique, wherein the image of the object is for a multi-slice computed tomography imaging system.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

Figure 1:
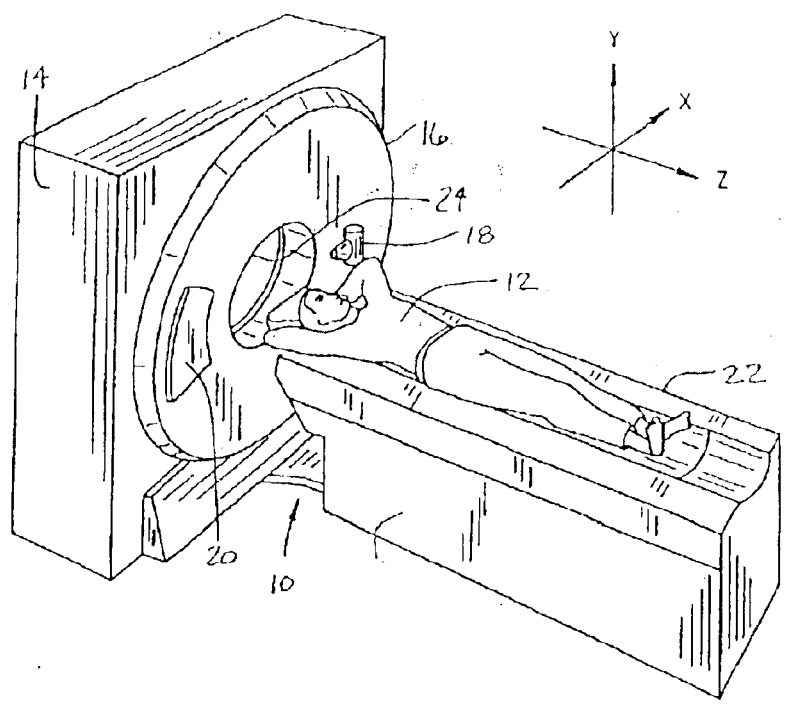
FIG. 1 is a pictorial view of a multi-slice helical scan CT imaging system utilizing a method of reconstructing an image in accordance with an embodiment of the present invention.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "image space" refers to a set of vectors arranged in an array for use with a method of the present invention. The array may be of any number of dimensions, such as two-dimensional, three-dimensional, four-dimensional, etc. An example of an image space that may be used in a method of the present invention is a set of all possible images representable on a lattice of a given dimension. A single element (vector) of the set of the image space may be viewed on a visual display apparatus to allow a user to gain information of the interior of a scanned object.

For the purposes of the present invention, the term "forward model" refers to a description of the transformation from the image space of a scanned object to the projection space for a scanned object, as modeled after the operation of the CT imaging system. The operation of the forward model on an image vector is referred to as "forward projection."

For the purposes of the present invention, the term "computed tomography model" refers to a mathematical description of the relation between a vector in the image space and a vector in the projection space. A computed tomography model includes a forward model and a cost function chosen to evaluate the closeness of a match between a projection vector and a forward projection of an image vector by a forward model.

For the purpose of the present invention, the term "projection space" refers to a set of vectors of integral X-ray attenuation values. The vectors that make up a projection space may comprise data from an X-ray CT scanner. Also, the vectors that make up a projection space may be forward projections of vectors from an image space.

For the purposes of the present invention the term "visual display device" refers to any type of device such as a CRT monitor, LCD screen, projected image, etc. used to visually inspect multidimensional vectors.

For the purposes of the present invention, the term "multi-slice computed tomography imaging system" refers to an X-ray CT scanner in which a detector array contains multiple rows of detectors, each row displaced from all other rows in the direction of the axis of the system about which the gantry rotates.

For the purposes of the present invention, the term "filtered backprojection" refers to a technique of reconstructing images from projection data by processing data in the projection space, then forming the value of each element in the image space as a linear combination of values from processed data, those values taken from projection space points to which the given image element contributes in forward projection. Filtered backprojection techniques are described in such places as Avinash C. Kak and Malcolm Slaney, "Principles of Computerized Tomographic Imaging," Classics in Applied Mathematics, 33, SIAM, 2001, ISBN:089871494X, the entire contents and disclosure of which is hereby incorporated by reference.

For the purposes of the present invention, the term "high quality reconstruction image" refers to an image space vector whose accuracy as a representation of the object under study is comparable to those produced by currently available commercial CT imaging systems and known in the art.

Description

While the present invention is described with respect to apparatus and methods of reconstructing an image using iterative techniques for a multi-slice computed tomography (CT) imaging system, the following apparatus and method are capable of being adapted for various purposes including, but not limited to the following applications: magnetic resonance imaging (MRI) systems, CT systems, radiotherapy systems, X-ray imaging systems, ultrasound systems, nuclear imaging systems, magnetic resonance spectroscopy systems, and other applications known in the art.

In the following description, various operating parameters and components are described for one constructed embodiment. These specific parameters and components are included as examples and are not meant to be limiting.

Referring now to FIG. 1, a pictorial view of a multi-slice CT imaging system 10, utilizing a method of reconstructing an image of medical patient 12 in accordance with an embodiment of the present invention, is shown. Imaging system 10 includes a gantry 14 that has a rotating inner portion 16 containing an x-ray source 18 and a detector array 20. X-ray source 18 projects a beam of x-rays toward detector array 20. Source 18 and detector array 20 rotate about an operably translatable table 22. Table 22 is translated along the z-axis between source 18 and detector 20 to perform a helical scan. The beam, after passing through medical patient 12, within a patient bore 24, is detected at detector array 20 to generate projection data that is used to create a CT image.

Figure 2:
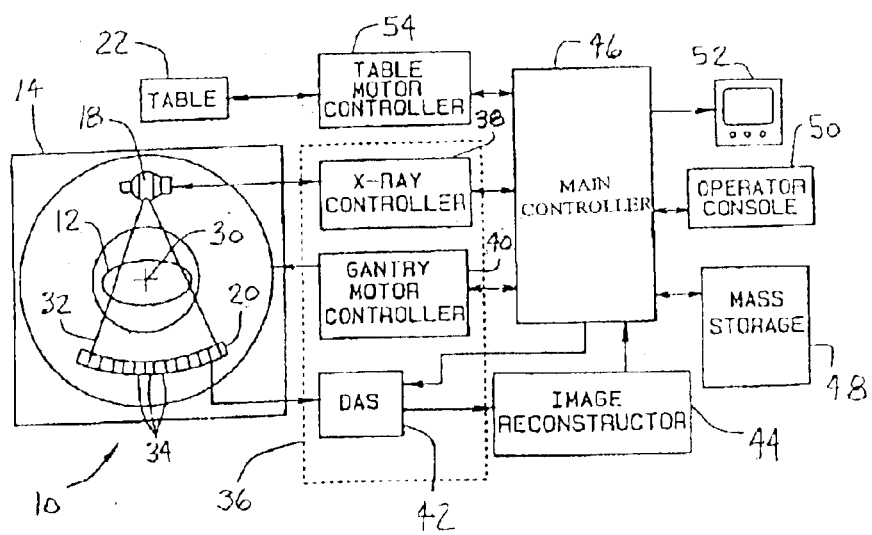
FIG. 2 is a block diagrammatic view of the multi-slice helical scan CT imaging system in accordance with an embodiment of the present invention.

Referring now to FIG. 2, a block diagrammatic view of system 10 in accordance with an embodiment of the present invention, is shown. Source 18 and detector array 20 rotate about a center axis 30. Beam 32 is received by multiple detector elements 34 in multiple detector rows. Each detector element 34 generates an electrical signal corresponding to the intensity of an impinging x-ray beam. As beam 32 passes through patient 12, beam 32 is attenuated. Rotation of the center portion of the gantry and the operation of source 18 are governed by a control mechanism 36. Control mechanism 36 includes an x-ray controller 38 that provides power and timing signals to source 18 and a gantry motor controller 40 that controls the rotational speed and position of the center portion of the gantry. A data acquisition system (DAS) 42 samples analog data from detector elements 34 and converts the analog data to digital signals for subsequent processing. An image reconstructor 44 receives sampled and digitized x-ray data from DAS 42 and performs high-speed image reconstruction. A main controller 46 stores the CT image in a mass storage device 48.

Main controller 46 also receives commands and scanning parameters from an operator via an operator console 50. A display 52 allows the operator to observe the reconstructed image and other data from main controller 46. The operator supplied commands and parameters are used by main controller 46 in operation of DAS 42, x-ray controller 38, and gantry motor controller 40. In addition, main controller 46 operates a table motor controller 54, which translates table 22 to position patient 12 in gantry 14.

X-ray controller 38, gantry motor controller 40, image reconstructor 44, main controller 46, and table motor controller 54 are preferably based on micro processors, such as a computer having a central processing unit, memory (RAM and/or ROM), and associated input and output buses. X-ray controller 38, gantry motor controller 40, image reconstructor 44, main controller 46, and table motor controller 54 may be a portion of a central control unit or may each be stand-alone components as shown.

Figure 3:
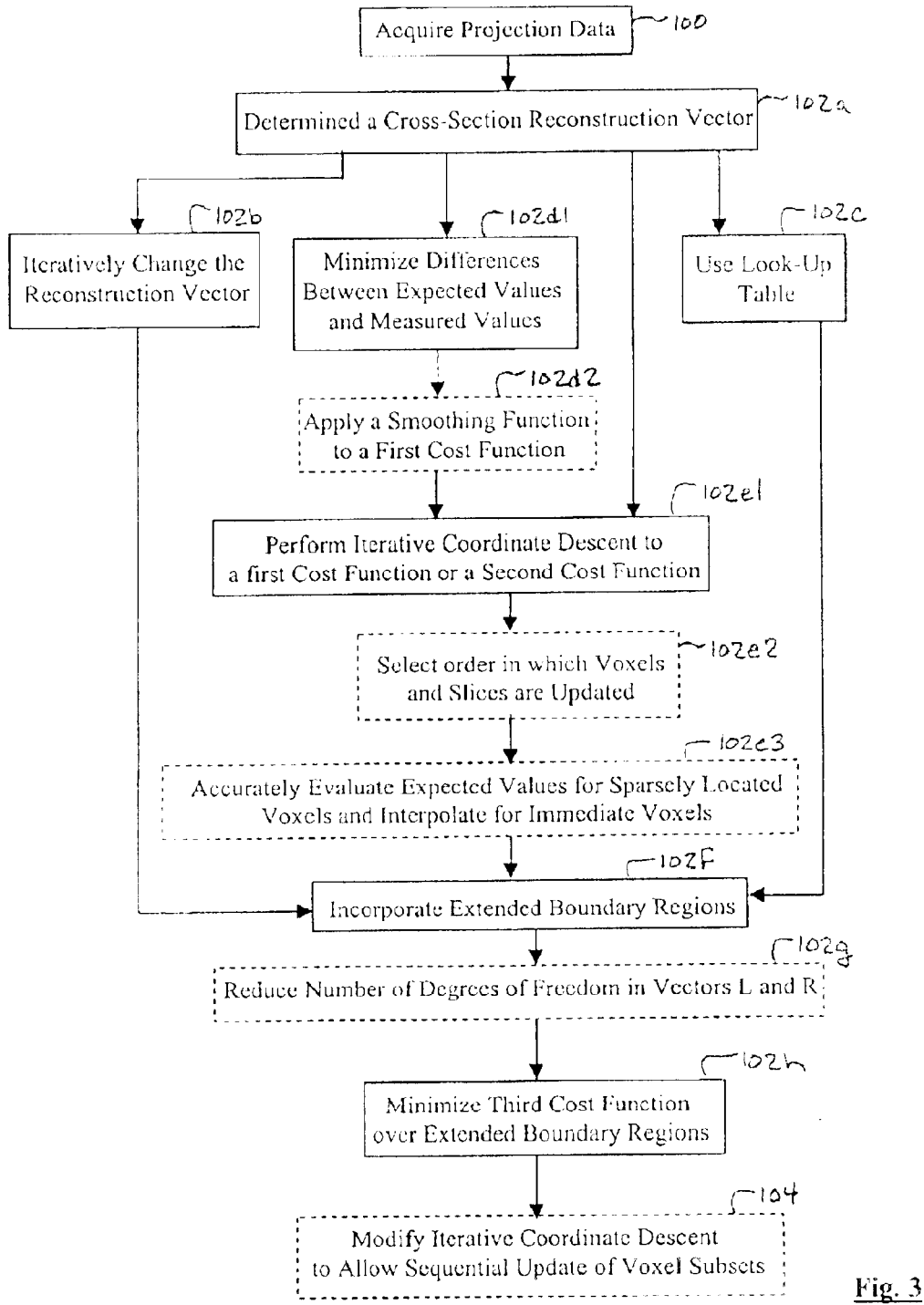
FIG. 3 is a logic flow diagram illustrating a method of reconstructing an image of an object for a multi-slice computed tomography imaging system in accordance with an embodiment of the present invention.

Referring to FIG. 3, a logic flow diagram illustrating a method of reconstructing an image of patient 12 for a multi-slice CT imaging system in accordance with an embodiment of the present invention is shown.

In step 100, system 10 helically scans an object to acquire projection data. The detector array generates projection data upon receiving the x-ray beam from the source.

Figure 4:
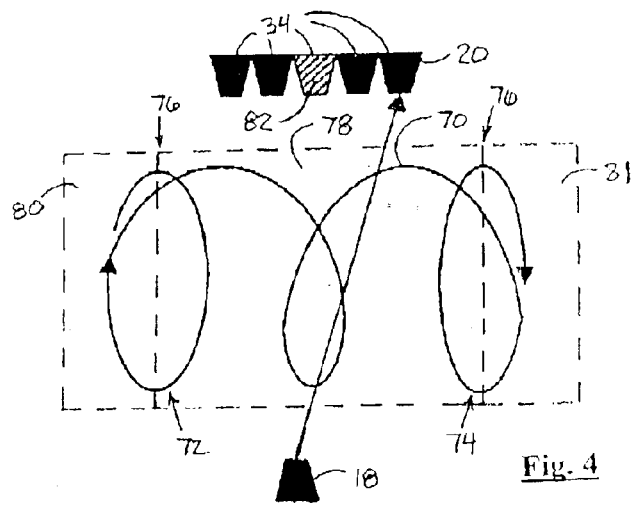
FIG. 4 is a representation of a scan including cine mode scans of boundary regions and a helical scan for an intermediate region, with a two-dimensional field of view and corresponding extended boundary regions in accordance with an embodiment of the present invention.

Referring now to FIGS. 3 and 4, in FIG. 4 a helical trajectory 70 is shown which is designed to eliminate or reduce boundary effects in accordance with an embodiment of the present invention. Helical scan pitch may be adjusted during the helical scanning. By adjusting helical scan pitch, helical scan pattern is adjusted, decreasing difficulty in handling boundary conditions. The scan pitch may be adjusted at a beginning 72 of a scan series and at an end 74 of a scan series to provide boundary regions 76 of a FOV 78 that either eliminate or reduce the size of extended boundary regions 80 and 81. Setting the pitch equal to zero at boundary regions 76 is referred to as cine or step-and-shoot data acquisition mode. Regions 80 and 81 have zero width when only center detectors 82 of detector array 20 are used. When all detectors 34 are used in cine mode, regions 80 and 81 have a width greater than zero with reduced size relative to the size of regions 80 and 81 in normal full helical mode.

In steps 102–104, a CT modeled iterative reconstruction technique is performed to reconstruct the image in response to projection data.

In step 102a, image reconstructor 44 determines a cross-section reconstruction vector, which approximately matches the projection data via a first CT model as shown in equation 1.

$$y_n = F(\hat{x}, \theta_n, z_n) \tag{1}$$

In performing iterative reconstruction, system 10 is modeled by the function $F(\hat{x},\theta_n,z_n)$ that describes expected output for each detector 34 at each rotation angle θ and z position. Vector $\hat{x}$ contains a three-dimensional reconstruction of a portion of patient 12 in a plane of reconstruction. Values of vector $\hat{x}$ are determined from known values of $y_n$, $\theta_n$, and $z_n$. Rotation angles $\theta_n$, and z-axis positions $z_n$ correspond to an $n^{th}$ detector measurement or frame. Measured values $y_n$ and expected values $F(\hat{x},\theta_n,z_n)$ are compared for each $n^{th}$ frame.

To determine the vector $\hat{x}$, the present invention determines the contribution of each voxel of an image space to each data point of the projection data. A voxel is a volume element, as known in the art, that refers to a value of an object at a particular position in space. The vector $\hat{x}$ is determined such that equation 1 is satisfied, or in other words, a vector $\hat{x}$ is determined that approximately matches the projection data. Solving equation 1 eliminates traditional interpolation and artifacts that may be caused thereby.

In step 102b, vector $\hat{x}$ may be determined using various methods including iteratively changing vector $\hat{x}$ so that error in equation 1 is reduced. For example, algebraic reconstruction techniques, known in the art, may be used to iteratively change sub-sets of values of vector $\hat{x}$ to reduce error.

In step 102c, the cross-section reconstruction vector $\hat{x}$ may be determined using a first look-up table to determine and account for source-to-detector radiation transfer to voxels at particular locations.

In step 102d1, another method of determining vector $\hat{x}$ is performed by minimizing differences between expected values $F(\hat{x},\theta_n,z_n)$ and measured values $y_n$ by computing a solution to the first CT model within a first cost function of equation 2.

$$\hat{x} = \operatorname*{argmin}_{x} \sum_{n=0}^{m} D[y_n - F(x, \theta_n, z_n)] \tag{2}$$

The first cost function is summed over the number of frames m and D represents a general non-negative distortion measure. For example, distortion measure D may be a quadratic error term, as in equation 3.

$$D[v] = v'Bv \tag{3}$$

In equation 3, distortion measure D is a scalar that is set equal to a transpose of a vector v multiplied by a positive definite matrix B and by a vector v. Distortion measure D may include non-negative convex functions, negative logarithms of probability density functions, and other penalty functions. Equation 2 may be expressed with a quadratic form for D as shown in equation 4.

$$\hat{x} = \operatorname*{argmin}_{x} \sum_{n=0}^{m} \|y_n - F(x, \theta_n, z_n)\|^2 \tag{4}$$

In step 102d2, when minimizing the difference between expected projections and measured projections, the first cost function may be augmented by a smoothing function to form a second cost function of equation 5. Equation 6 is a quadratic form of equation 5.

$$\hat{x} = \operatorname*{argmin}_{x} \left\{ \sum_{n=0}^{m} D[y_n - F(x, \theta_n, z_n)] + S(x) \right\} \tag{5}$$

$$\hat{x} = \operatorname*{argmin}_{x} \left\{ \sum_{n=0}^{m} \|y_n - F(x, \theta_n, z_n)\|^2 + S(x) \right\} \tag{6}$$

S(x) is a positive smoothing function, which is selected to be relatively large when the shape of vector $\hat{x}$ is not smooth and relatively small when shape of vector $\hat{x}$ is smooth.

In step 102e1, the cross-section reconstruction vector $\hat{x}$ may also be determined using iterative coordinate descent (ICD) to minimize the first cost function or the second cost function.

Figure 5:
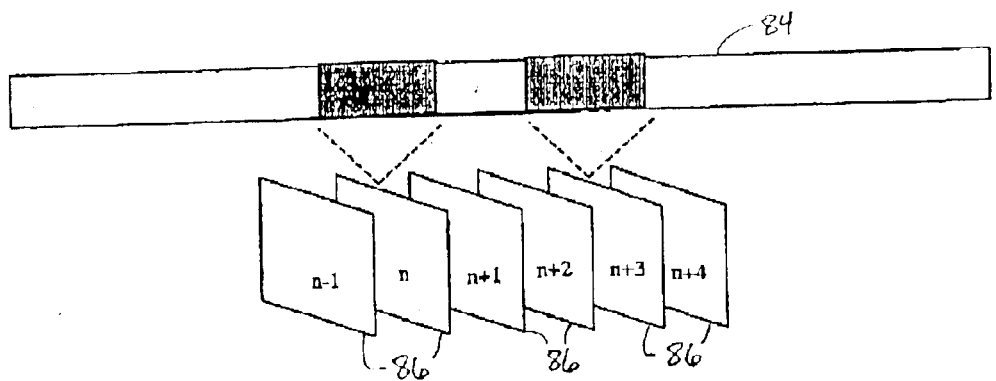
FIG. 5 is a perspective view of parallel data access in accordance with an embodiment of the present invention.

Referring now to FIGS. 3 and 5, in FIG. 5 a perspective view of parallel data access in accordance with an embodiment of the present invention is shown. Projection data 84 is divided into sets necessary for separate reconstructed slices 86. ICD may be initiated with a high quality initial reconstruction image. The high quality initial reconstructed image preferably has accurate representation of the low spatial frequencies in the image, since ICD iterations rapidly correct inaccuracies in the reconstruction at high spatial frequencies. Filtered backprojection is a desirable initial reconstruction because it accurately represents the low frequency content in the reconstruction. There are several methods of presenting initial images for faster convergence. For example, results of slice n may be used as an initial condition for slices n−1 and n−1. Alternatively, a low resolution reconstruction may first be computed, and then it may be interpolated for use as an initial reconstruction at a higher resolution. This process of reconstruction and interpolation may be repeated starting at very coarse resolutions, and completing at a finest desired resolution.

In step 102$e2$, speed and memory requirements of ICD may also be improved by appropriately selecting the order in which voxels and slices are updated. Slices may be accessed in lexicographic order, serpentine order, progressive order, pseudo-random order, or in another applicable order known in the art. ICD minimizes a cost function by sequentially updating each voxel. Each voxel is updated to minimize the first cost function or the second cost function while maintaining constant values for other voxels.

The CT model is preferably an accurate representation of geometric and physical relationships of components in system 10. The CT model may be derived from experimentation, modeling of the source and detector response physics, or computer simulation.

In step 102$e3$, for computational efficiency, form of contribution of each of a set of sparsely located voxels to the expected values $F(\hat{x},\theta_n,z_n)$ may be accurately evaluated, with the forms of these contributions then interpolated for immediate voxels. Source-to-detector radiation transfer to voxels at particular locations may be represented by a second look-up table of values that are indexed by relative positions and orientations of source-detector-voxel. The second look-up table is referred to as a point-spread-function, since it specifies spread of a point voxel influence on nearby detectors.

Figure 6:
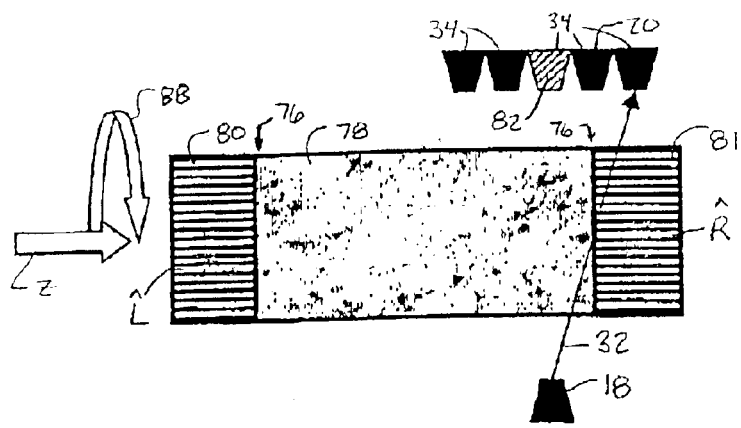
FIG. 6 is a two-dimensional field of view and corresponding extended boundary regions in accordance with an embodiment of the present invention.

Referring now to FIGS. 3 and 6, in FIG. 6 a two-dimensional field of view 78 and corresponding extended boundary regions 80 and 81 are shown in accordance with an embodiment of the present invention. Helical scan rotation is illustrated by arrow 88. Mathematically, density of material in extended boundary regions 80 and 81 affects the measured values $y_n$ for frames n near boundaries 76, but is not accounted for in the function $F(\hat{x},\theta_n,z_n)$ if regions 80 and 81 are not included in x. Therefore, artifacts exist in reconstruction of slices near beginning 72 and end 74 along the z-axis. Steps 102$h$–104 minimize the boundary artifacts by incorporating extended boundaries 80 and 81, which are used to estimate effects of boundary regions 76, represented by extended boundary vectors $\hat{L}$ and $\hat{R}$. Vectors $\hat{L}$ and $\hat{R}$ account for distortions produced by absorption in the extended boundary regions 80 and 81.

In step 102$f$, extended boundary regions 80 and 81 are incorporated within the first CT model to form a second CT model in a third cost function of equation 7 and in quadratic form in equation 8.

$$\hat{x} = \underset{x}{\arg\min}\underset{R,L}{\min}\left\{\sum_{n=0}^{m} D[y_n - F(x, R, L, \theta_n, z_n)] + S(x)\right\} \quad (7)$$

$$\hat{x} = \underset{x}{\arg\min}\underset{R,L}{\min}\left\{\sum_{n=0}^{m} \|y_n - F(x, R, L, \theta_n, z_n)\|^2 + S(x)\right\} \quad (8)$$

In step 102$g$, the time required to perform minimization of step 102$f$ may be decreased and accuracy may be increased by reducing the number of degrees of freedom in vectors $\hat{L}$ and $\hat{R}$. For instance, extended boundaries 80 and 81 may be represented using lower resolution in regions of less importance. The extended boundaries 80 and 81 may be sampled more finely near boundary regions 76 and more coarsely at points further from the FOV 78 within regions 80 and 81. The reduction in sampling resolution may be achieved by increasing size of voxels along the z-axis, or in directions perpendicular to the z-axis, or in any combination of directions. Regions 80 and 81 may be represented by a single slice in which each voxel extends to a full extent of regions 80 and 81. In other words, the reconstructed object may be assumed constant along the z-axis in regions 80 and 81.

As an option to step 102$f$, the extended boundary reconstruction images may be determined using filtered backprojection or other reconstruction technique known in the art in order to provide an approximate estimation of the object in regions 80 and 81. The values of regions R and L are not changed during the CT modeled iterative reconstruction technique.

In step 102$h$, the third cost function is minimized over the regions 80 and 81 with or without incorporation of a smoothing function S(x), its presence depending on whether step 102$d2$ is performed above during the CT modeled iterative reconstruction technique.

In step 104, the ICD may be modified to allow sequential update of voxel subsets. The voxel subsets may include sub-regions, sparsely sampled sub-regions, or individual two-dimensional slices of a reconstructed volume. Updating of voxel subsets may improve convergence speed and allow for parallel computation. Each slice of the reconstructed volume accesses a limited range of the helical scan dataset; therefore, slices that are separated by sufficient distance may be processed independently since they do not access or process the same projection measurement data or image plane variables.

The above-described steps are meant to be an illustrative example; the steps may be performed synchronously or in a different order depending upon the application.

The present invention provides a multi-slice CT imaging system and method of reconstructing a CT image using iterative reconstruction while minimizing artifacts. The present invention accounts directly for geometry of the multi-slice CT imaging system and for extended boundary regions further preventing artifacts and blurring of a reconstructed image.

The above-described apparatus and manufacturing method, to one skilled in the art, is capable of being adapted for various purposes including, but not limited to applications including MRI systems, CT systems, magnetic resonance spectroscopy systems, and other applications known in the art. The above-described invention may also be varied without deviating from the true scope of the invention.

All documents, patents, journal articles and other materials cited in the present application are hereby incorporated by reference.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An imaging system comprising:

a source generating an x-ray beam;

a detector array receiving said x-ray beam and generating projection data;

a translating table having an object thereon and operable to translate in relation to said source and said detector array;

said source and said detector array rotating about said translating table to helically scan said object;

an image reconstructor electrically coupled to said detector array and reconstructing an image in response to said projection data using a computed tomography modeled iterative reconstruction technique comprising determining a cross-section reconstruction vector, which approximately matches said projection data via a computed tomography model, wherein said imaging system is a multi-slice computed tomography imaging system.

2. The system of claim 1, wherein said image reconstructor in reconstructing an image determines a cross-section reconstruction vector which approximately matches said projection data via said computed tomography model.

3. The system of claim 1, wherein said image reconstructor in determining a cross-section reconstruction vector applies a smoothing function within said computed tomography model.

4. The system of claim 1, wherein said image reconstructor in determining a cross-section reconstruction vector incorporates extended boundary regions into said computed tomography model.

5. A method of reconstructing an image of an object comprising:

providing projection data; and performing a computed tomography modeled iterative reconstruction technique to reconstruct the image in response to said projection data comprising determining a cross-section reconstruction vector, which approximately matches said projection data via a computed tomography model, wherein said reconstructed image of said object is for a multi-slice computed tomography imaging system.

6. The method of claim 5, wherein said projection data is acquired by helically scanning the object.

7. The method of claim 6, further comprising adjusting helical scan pitch during said helical scanning.

8. The method of claim 5, further comprising determining extended boundary reconstruction images using filtered backprojection.

9. The method of claim 5, wherein determining a cross-section reconstruction vector further comprises incorporating extended boundary regions into said computed tomography model.

10. The method of claim 9, further comprising minimizing a cost function over said extended boundary regions during said iterative reconstruction technique.

11. The method of claim 5, further comprising reducing number of degrees of freedom in extended boundary vectors.

12. The method as in claim 5, wherein said computed tomography modeled iterative reconstruction technique comprises iteratively changing said cross-section reconstruction vector.

13. The method of claim 12, wherein iteratively changing said cross-section reconstruction vector comprises using an algebraic reconstruction technique.

14. The method of claim 5, wherein determining said cross-section reconstruction vector comprises minimizing difference between expected projections and measured projections.

15. The method of claim 14, wherein minimizing difference between expected projections and measured projections comprises applying a smoothing function within said computed tomography model.

16. The method of claim 5, wherein determining said cross-section reconstruction vector comprises using a look-up table to determine and account for source-to-detector radiation transfer to voxels at particular locations of said reconstructed image.

17. The method of claim 5, wherein determining said cross-section reconstruction vector comprises using iterative coordinate descent to minimize a cost function.

18. The method of claim 17, further comprising sequentially updating voxel subsets of said reconstructed image.

19. The method of claim 17, further comprising initiating iterative coordinate descent with a high quality reconstruction image using filtered backprojection.

20. The method of claim 17, further comprising selecting an order in which voxels and slices are updated.

21. A method of reconstructing an image comprising:

helically scanning the object to acquire projection data; and performing a computed tomography modeled iterative reconstruction technique to reconstruct the image in response to said projection data comprising;

determining a cross-section reconstruction vector, which approximately matches said projection data via a computed tomography model;

incorporating extended boundary regions into said computed tomography model; and minimizing a cost function over said extended boundary regions during said iterative reconstruction technique, wherein said image of said object is for a multi-slice computed tomography imaging system.

22. The method of claim 21, wherein said projection data is acquired by helically scanning the object to acquire projection data.

* * * * *